United States Patent
Murray

(12) United States Patent (10) Patent No.: US 6,432,117 B1
Murray (45) Date of Patent: Aug. 13, 2002

(54) EAR CLEANING DEVICE

(76) Inventor: Jonathan Aidan Muir Murray, 7 Pampas Road, Smiths Bermuda FL05 (GB)

( * ) Notice: Subject to any disclaimer, the term of this patent is extended or adjusted under 35 U.S.C. 154(b) by 0 days.

(21) Appl. No.: 09/464,320

(22) Filed: Dec. 16, 1999

(51) Int. Cl.[7] ................................................ A61F 11/00
(52) U.S. Cl. ..................................................... 606/162
(58) Field of Search ................................ 606/161, 162; 604/1

(56) References Cited

U.S. PATENT DOCUMENTS

| 1,450,612 A | | 4/1923 | Schultz |
| 4,785,796 A | * | 11/1988 | Mattson |
| 5,888,199 A | * | 3/1999 | Karell et al. ................. 606/162 |

FOREIGN PATENT DOCUMENTS

| DE | 9308737.3 | 9/1993 |
| EP | 184237 | 6/1986 |
| EP | 744168 | 11/1996 |
| FR | 2531626 | 2/1984 |
| WO | WO 98/42284 | 10/1998 |

* cited by examiner

*Primary Examiner*—Michael H. Thaler
(74) *Attorney, Agent, or Firm*—John N. Bain; Raymond J. Lillie

(57) ABSTRACT

A probe element with helical grooves is dimensioned to be inserted into the ear canal and stop short of the ear drum, the element being made of soft compressed cotton. A bulbous flexible plastic handle has an interior rod and a clutch for releasably receiving the element. Depressing the handle at the rod location forming an ejection button displaces the rod and an interior-coupling member for ejecting the probe element. The rigid smooth handle is rotated a quarter turn to remove wax from the ear canal. The element extends from the handle a predetermined length to not engage the eardrum, the handle having a blunt tip acting as a stop for the element during insertion.

19 Claims, 2 Drawing Sheets

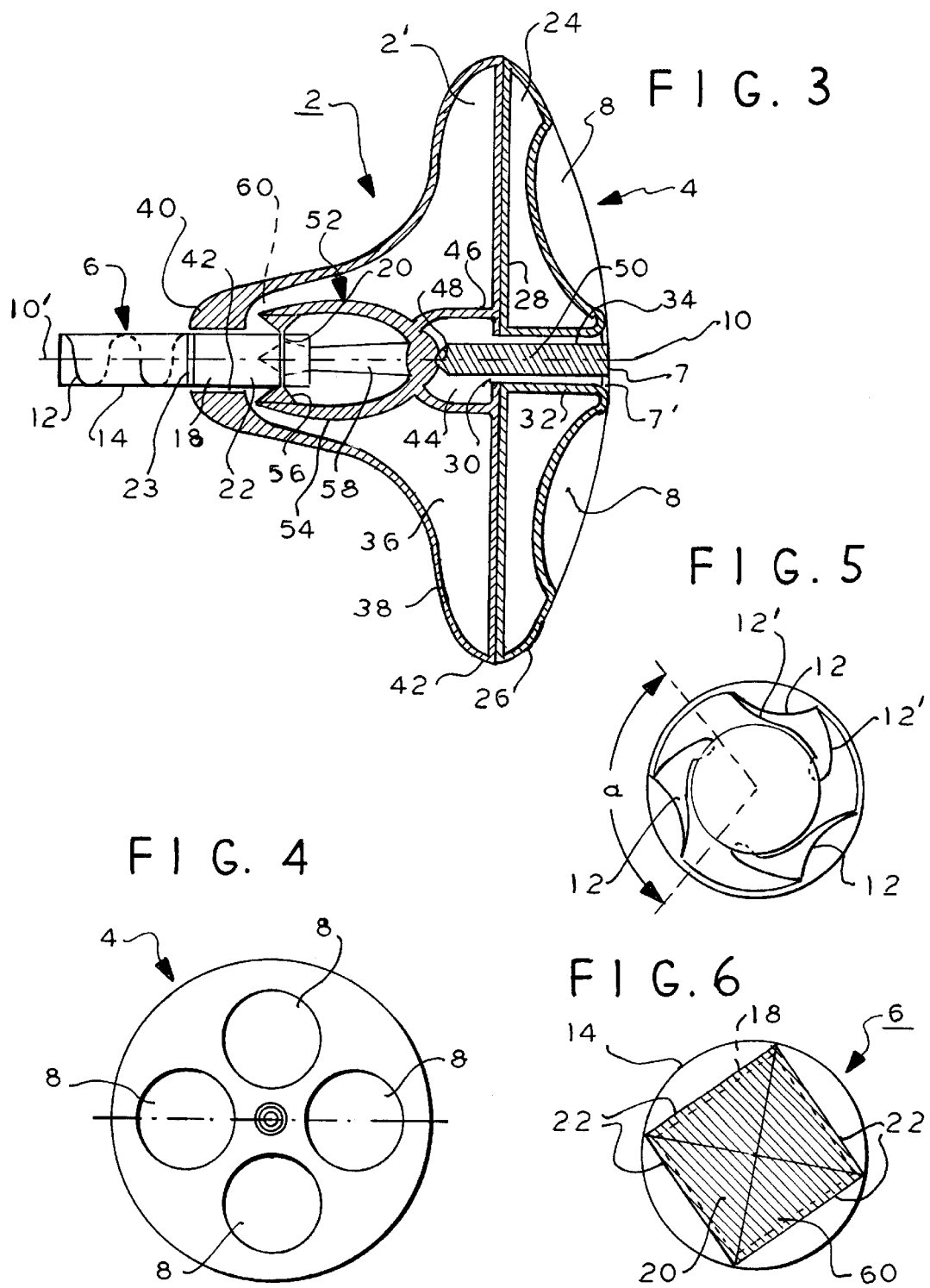

EAR CLEANING DEVICE

This invention relates to devices for cleaning wax from the ear.

Ear cleaning is a major problem because the outer ear contains delicate tissue that is readily damaged. The present invention is a recognition of the need for a device that is readily adapted to clean ears of wax while structurally and functionally limiting the distance between the end of the distal end of the device and the ear drum when inserted into the outer ear canal to avoid damage to either the ear drum or delicate tissue in the vicinity thereof. The device of the present invention avoids forcing ear wax deeper into the outer ear canal or creating a massive accumulation of ear wax occluding the inner portions of the outer ear canal.

A device for cleaning wax from the human ear according to the present invention comprises a probe element having a longitudinal axis and adapted for harmless insertion into the outer ear canal for removing wax from the outer ear canal; and a handle for releasably securing the element thereto which structurally limits the distance between the distal end of the element from the innermost portion of the outer ear canal proximal to the car drum and for manually inserting the element into the outer ear canal and for manually rotating the element to remove ear wax.

In one aspect, the probe element comprises a tapered elongated shank having a helix groove along the exterior surface thereof and extending along said axis. Preferably there are a plurality of said grooves spaced about the probe element, and more preferably three grooves each having an arc along the axis and about the axis at an angle of about 120° about the axis.

In a further aspect the handle is a generally rigid, smooth, hollow and dome-shaped.

In a further aspect, the device includes an ejection member secured to the handle and coupled to the probe element for selectively ejecting the probe element from the handle.

In a further aspect, the probe element and handle are dimensioned and arranged so that the inward movement of the probe element stops prior to engagement with the ear drum with the handle generally abutting the external ear of the person. Preferably, the probe element has a tapered ear cleaning operative portion and a cylindrical connector portion and more preferably, the element is compressed cotton.

Preferably, the handle and probe element include means for snap releasably connecting the element to the handle.

Preferably the handle is a rigid and externally smooth hollow dome, and more preferably, the dome has a gradually tapering snub nose portion having a bore which preferably has a generally square cross-section for receiving the probe element and a gripping rib in communication with the bore, said element having a connector portion with an annular groove for releasable engagement with the bore and rib. Preferably, the dome has a further bore for receiving the ejection member, the ejection member comprising a rod slidably mounted in the further bore, and an ejection button in the center of the dome operatively engageable with the end of the rod to axial slidably move the rod against the element to eject the element from the snub-nosed portion when the ejection button is depressed.

In a further aspect, the rod is dimensioned to abut the probe element at one rod end and the interior of the dome region distal the element, the dome including a flexible membrane over the ejection button of the rod end at the dome distal region. The dome preferably is rigid molded thermoplastic material. Preferably the dome is compartmentalized with a first compartment proximal said element and a second compartment distal the element separated by a transverse inner wall.

In a further aspect, the handle and probe element are dimensioned to automatically space the element from the inner ear when the handle abuts the outer surface of the ear.

In a further aspect, the device includes an intermediate ejection member coupled in the interior of the dome between the element and the rod the interior ejection member for displacement of the element in response to an element ejection displacement of the rod.

IN THE DRAWING

FIG. 3 is a side elevation diagrammatic sectional view of the device of FIG.

FIG. 4 is an end view of the handle of the device of FIG. 1;

FIG. 5 is an end elevation view of the probe element at the cleaning end of the device of FIGS. 1 and 3; and FIG. 6 is an end elevation view of the probe element at the connector end of the device of FIGS. 1 and 3, opposite the cleaning end shown of FIG. 5.

Figure 1:
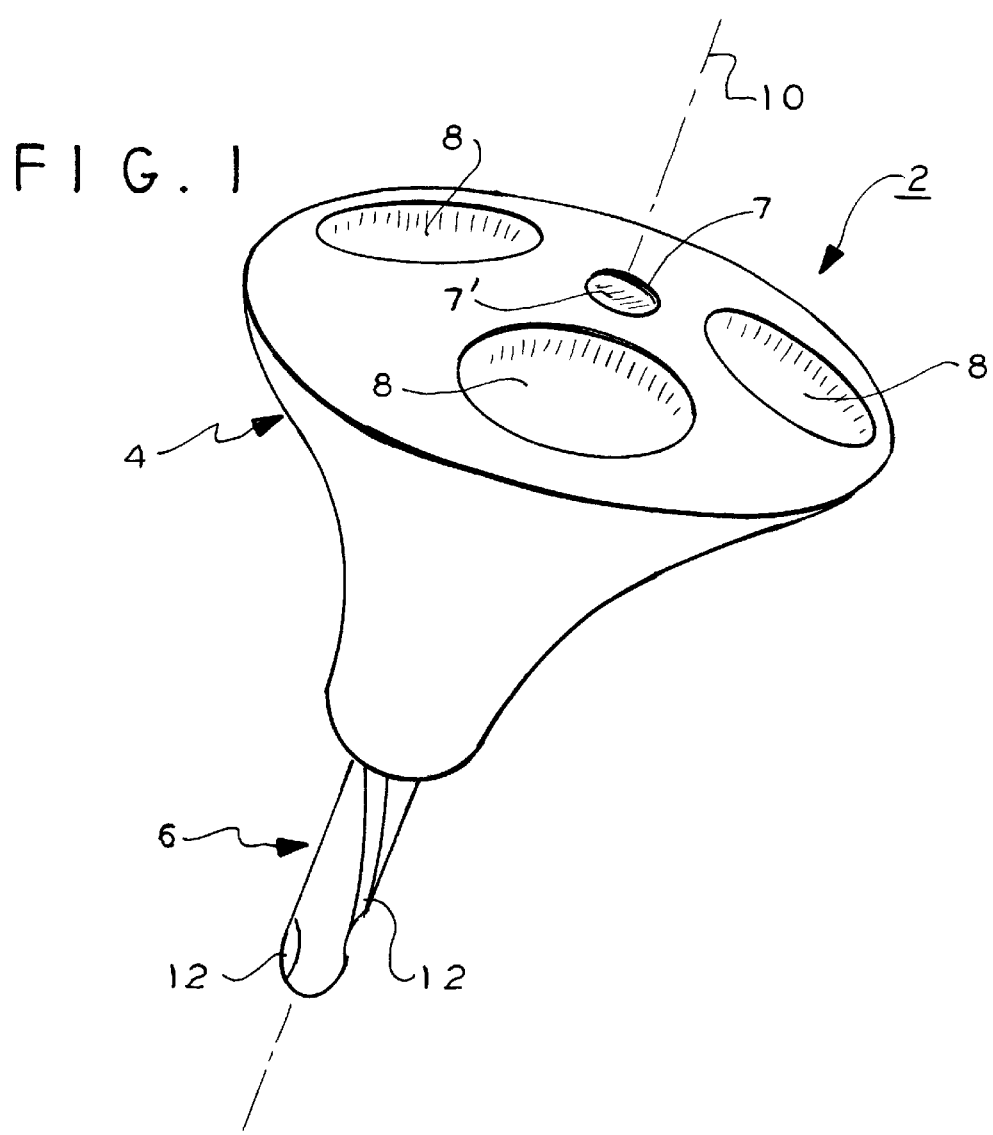
FIG. 1 is a perspective view of an ear cleaning device according to an embodiment of the present invention.

In FIG. 1, ear cleaning device 2 comprises a generally dome-shaped handle 4 and a cleaning probe element 6. The handle 4 is a rigid externally smooth and molded from a suitable plastic material. The handle 4 has four molded semi-spherical concave cavities 8 (FIG. 4) (three being shown in FIG. 1). The cavities 8 receive the fingers of a user for assisting in rotating the dome handle 4 about axis 10 during cleaning of the user's ear canal without injuring the ear drum or forcing ear wax further into the ear canal to form a compacted mass potentially occluding the outer ear canal. An ejection button 7 is formed by a flexible membrane 7' in the handle 4 at the center of the external surface of the dome for selectively manually ejecting the probe element 6 after the cleaning process is completed through means hereinafter to be described.

Figure 2:
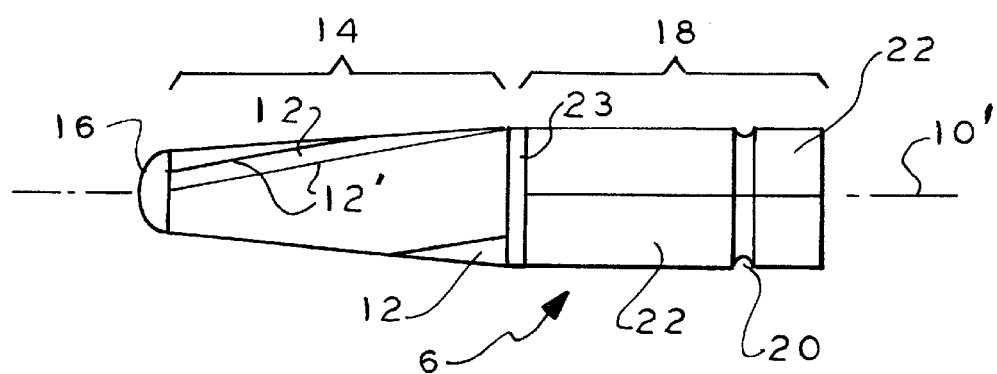
FIG. 2 is a side elevation view of an ear cleaning probe element used in the FIG. 1 embodiment.

The probe cleaning element 6 is made of cotton or other suitable material compressed in a conventional manner. The element 6 is sufficiently stiff to clean wax from the ear canal and sufficiently soft to do so without injury to the canal. The element has preferably three equally spaced identical parallel helix grooves 12 in the side thereof and extending along the axis 10. The grooves 12 preferably lie in an arcuate sector each of about 120°. The grooves 12 generally have parallel side edges 12'. In FIGS. 2 and 5, the clement 6 grooves 12 are identical and are equally spaced about the shank axis 10' of the element 6. The grooves 12 are in a frusto-conical tapered shank in region 14 of the element 6. Region 14 has an axial length preferably of about 12 mm. This is believed to be a common dimension for the depth of the ear canal of a human without engagement of the ear drum. That is, all persons are believed to have an ear canal depth somewhat greater than 12 mm so that no ear drum of any person randomly selected will be contacted by the element 6 for the length of the region 14. This is important to preclude damage to the ear drum and yet make the probe element fit for universal use.

The probe element 6 has a closed rounded end 16. Thus region 14 forms a snub nose section of the element 6. Preferably the rounded end has a diameter of about 3 mm and tapers to a maximum diameter of about 5 mm at portion 23 in this example. The rounded blunt end 16 further precludes damage to the ear canal. The element 6 has a connector portion 18, which is preferably square in cross-section as best shown in FIG. 6 formed by four flat sides. Connector portion 18 is provided with a continuous groove 20 extending about its entire periphery. Portions 14 and 18 are separated by an axial short circular cylindrical section 23.

In FIG. 3, handle 4 is a hollow dome. The handle 4 has a compartmentalized interior formed by relatively thin rigid side walls. A first compartment 24 is formed by the outer wall 26 of the handle and interior circular flat wall 28. Wall 28 has a central aperture 30. A rigid thin-walled tubular member 32 connects the wall 28 to membrane 7' on the outer surface of the handle 4. Member 32 forms an interior channel 34.

Wall 28 forms a second interior compartment 36 with the outer wall portion 38 of outer wall 26. Wall 38 tapers gradually and smoothly from rounded narrow tip 40 to its widest at wall 28. The taper of wall 38 is concave so that the blunt end at tip 40 is sufficiently large to abut the entry of a typical person's outer ear canal at its entrance without penetrating a significant distance into the outer ear canal. The rigid smooth blunt end at tip 40 serves as a gentle inward movement-limiting stop so that only the length of the grooved shank of the probe element 6 can enter the ear canal.

Wall 38 has a square bore 42 generally coaxial with and communicating with the end of the blunt tip 40 for closely receiving a portion of the square connector portion 18 of the probe element 6 that is adjacent to the probe element cylindrical shank section 23. Part of the connector portion 18 (FIG. 2) extends into the compartment 36.

A third internal compartment 44 is formed by wall 46. The wall 46 is relatively thicker on axis 10 where it joins with four generally flat walls 56. Wall 46 is provided with a recess 48 in the compartment 44. The compartment 44 is in communication with the passage 34. An ejection rod 50 is slidably mounted in channel 34 and has a projection that mates with and abuts wall 46 at recess 48. Passage 34 is thus fully enclosed.

A clutch 52 comprises four identical but separate walls 54, each of which is formed on and extends from wall 46 in compartment 36 toward tip 40. Walls 54 are flexible and curved as shown. A rib 56 is formed on and extends radially inwardly from the free ends of each of the walls 54. Each rib 56 engages a groove on one of the flat sides of the connector portion 18. The walls 54 are each radially outwardly resiliently deflectable such that each rib 56 snap-fits into and opposing and mating groove 20. The respective grooves 20 and mating ribs 56 cooperate to releasably hold the element 6 to the handle 4. The square sides of bore 42 hold the probe element 6 and in this way rotation of the handle 4 rotates the probe element 6.

An axially displaceable coupling member 58 is located within the enclosure defined by the walls 54 which is engaged to and couples the wall 46 on axis 10 to the probe element 6. The coupling member 58 and the rod 50 are both rigid and preferably formed from a suitable plastic material for transferring axial displacement of the rod 50 to the left in FIG. 3 to the element 6 on concentric axes 10. 10'. The member 58 has a pyramid-shaped recess 60, which receives a pyramid-shaped end on the coupling member 58. Thus depression of the ejection button formed by membrane 7' on the exterior of wall 26 on handle 4 axially displaces rod 34, coupling member 58 and probe element 6 snap-forcing the walls 54 outwardly thus disengaging element 6 from the handle 4. This eliminates the need for the user to touch the soiled element 6.

In operation, the user inserts a probe element 6 into the bore 42 until the ribs 56 on walls 54 snap engage with mating grooves 20 on the connector portion 18. The element 6 and the coupling member 58 are dimensioned such that the pyrimid-shaped tip engages in the mating recess 60 in the end of the probe element 6 when the ribs snap engage with the grooves 20. The probe element 6 is then inserted into the ear canal until the handle tip 40 engages the entrance to the outer ear canal while slowly rotating the handle 4. Alternatively, the probe element 6 may be fully inserted into the outer ear canal and then the handle 4 rotated a quarter turn after insertion. This removes the wax from the sides of the canal. The element 6 is then withdrawn from the ear canal and the ejection button 7 depressed, ejecting the element 6. Preferably, each probe element is discarded after one use.

An organic atomized spray solution may be used with the device 2 for dissolving wax. The spray has prophylactic qualities, and prevents wax accumulation.

The spray comprises by weight:

(a) approximately 10% to 30% olive oil. A suitable olive oil contains approximately 74% oleic acid, $C_3 (CH_2)_7 C=C(CH_2)COOH$), (b) approximately 20% to 30% acetic acid ($CH_3COOH$), and (c) approximately 20% to 40% isopropyl alcohol ($CH_3H_7OH$). The preferred spray composition consists of approximately 10% olive oil, approximately 70% acetic acid and approximately 20% isopropanol.

This solution has been clinically tested against ear drops, which are used for removal and the prevention of ear wax and indicated superior action to known ear drops. See paper submitted for publication in the *Journal Laryngology & Otology* by Dr. J. A. M. Murray. The ear spray reaches more areas of the ear canal than ear drops and is consequentially more effective. Ear drops are usually applied with the head of a person tilted and most ear drops run out when the head is returned upright.

The ear spray expels a gentle atomized spray and each pump releases the correct dosage for daily application. Wax accumulation can lead to deafness, tinnitus, ear ache and ear infection.

There is a problem with potential allergies to antibiotics presently in use in ear drops. There is also a resistance to organisms to the various antibiotics. Accumulation of wax irritates the skin of the external auditory meatus predisposing to dermatitis and infection, in turn which leads to edema (swelling) of the skin making cleaning of the canal more difficult. The daily use of the solution of the present invention obviates most of these problems.

The spray solution is preferably used before use of the ear-cleaning device described above. Additionally, the spray composition can be applied to the wax-removing element of the cleaning device described herein before its use in the ear. In order to maximize the prophylactic effect of period use of the spray, it should be employed directly into the ear and not just as applied to the cleaning element. There thus has been described an ear cleaning device comprising a dome shaped rigid, externally smooth hollow handle adapted for manual gripping. A rod is positioned in the dome for axial displacement upon compression of the ejection button. A clutch is located within the interior of the dome. A snub nose is formed as part of the dome and has a probe element-receiving bore in communication with the clutch. An ear cleaning probe element is releasably secured in a bore in the nose by the clutch, the probe having a tapered configuration with helical grooves extending axially along the external surface thereof and dimensioned to be inserted in the ear canal and clean wax from the sides of the canal without impingement upon the ear drum, the element being located to be responsive to axial displacement of the rod to eject the element from the nose in response to the displacement.

It will occur to one of ordinary skill that various modifications may be made to the disclosed device, which is given by way of illustration and not limitation. It is intended that the scope of the invention be as defined in the appended claims.

What is claimed is:

1. A device for cleaning wax from the human ear, comprising:
   a probe element having a longitudinal axis and adapted for harmless insertion into the ear cavity for removing wax from the sides of the cavity;
   a handle for releasably securing said probe element thereto for automatic harmless spacing from the inner ear and for inserting said probe element manually into the cavity and rotating said probe manually for said removing of said wax; and
   an ejection member secured to said handle and coupled to said probe element for selectively ejecting said probe element from said handle.

2. The device of claim 1 wherein said probe element comprises a tapered elongated shank having at least one helical groove along the exterior surface thereof and extending along said axis.

3. The device of claim 2 wherein said shank includes a plurality of said helical grooves spaced about said probe element.

4. The device of claim 3 wherein said shank has three helical grooves, wherein each groove has an arc along said axis and about the axis at an angle of about 120° about the axis.

5. The device of claim 1 wherein said handle is a rigid, smooth, hollow dome.

6. The device of claim 5 wherein said dome has a gradually tapering snub nose portion having a bore for receiving said probe element and a gripping rib in communication with said bore, said element having a connector portion with an annular groove for releasable engagement with the bore and rib.

7. The device of claim 6 wherein said dome has a second bore for receiving said ejection member, said ejection member comprising a rod in said second bore, and an ejection button to displace the rod axially against said probe element to eject said probe element from said snub portion when the ejection button is compressed.

8. The device of claim 7 wherein said rod has proximal and distal ends, said rod being contained in an interior channel in said dome, said rod being dimensioned to have the proximal end about an interior flexible membrane in the dome for displacement of the probe element at the rod end, said dome including an exterior flexible membrane enclosing the interior channel and over the rod at the distal end.

9. The device of claim 7, and further comprising an axially displaceable coupling member coupled in the interior of said dome between said ejection element and said rod.

10. The device of claim 1 wherein said probe element and said handle are dimensioned and arranged such that said probe element stops prior to engagement with the ear drum with said handle abutting the ear of the person.

11. The device of claim 1 wherein said probe element has a tapered ear cleaning operative portion and a cylindrical connector portion.

12. The device of claim 1 wherein said probe element is formed from compressed cotton.

13. The device of claim 1 wherein said handle and said probe element each include means for releasably connecting said element to said handle.

14. The device of claim 1 wherein said dome is formed from a rigid molded thermoplastic material.

15. The device of claim 14 wherein said dome is compartmentalized with a first compartment proximal to said probe element and a second compartment distal to the probe element, said first compartment and said second compartment being separated by a transverse inner wall.

16. The device of claim 1, and further comprising a resilient clutch for releasably securing said probe element to said handle, said handle comprising a rigid smooth molded hollow dome with a snub nose portion for receiving said probe element.

17. The device of claim 16 wherein said dome is rigid and has an interior channel compartment with rigid walls and an ejection rod in the compartment, said interior channel being coupled to said probe element such that axial displacement of said rod ejects said probe element from said handle.

18. The device of claim 1 wherein said handle and said probe element are dimensioned to space automatically said probe element from the inner ear when said handle abuts the outer surface of the ear.

19. The device of claim 1 wherein a composition consisting essentially of by weight approximately 10% to 30% olive oil, approximately 30% to 70% acetic acid and approximately 20% to 40% isopropyl alcohol is applied to said element before use.

* * * * *